United States Patent
Maillefer et al.

(10) Patent No.: US 7,399,479 B2
(45) Date of Patent: Jul. 15, 2008

(54) MICROEMULSIONS, ESPECIALLY FOR SKIN OR HAIR TREATMENT

(75) Inventors: Sarah Maillefer, Middes (CH); Daniel Chambettaz, St. Ursen (CH); Michael Franzke, Rossdorf (DE)

(73) Assignee: Wella AG, Darmstadt (DE)

( * ) Notice: Subject to any disclaimer, the term of this patent is extended or adjusted under 35 U.S.C. 154(b) by 349 days.

(21) Appl. No.: 11/047,116

(22) Filed: Jan. 31, 2005

(65) Prior Publication Data
US 2005/0170988 A1 Aug. 4, 2005

(30) Foreign Application Priority Data
Jan. 29, 2004 (DE) .................. 10 2004 004 394

(51) Int. Cl.
*A61K 31/385* (2006.01)
(52) U.S. Cl. .................. 424/401; 424/70; 510/137; 510/138; 510/407
(58) Field of Classification Search .................. None
See application file for complete search history.

(56) References Cited
U.S. PATENT DOCUMENTS

| | | | |
|---|---|---|---|
| 5,490,982 A | | 2/1996 | Siciliano |
| 6,074,996 A | * | 6/2000 | Elliott et al. ................. 510/125 |
| 6,497,866 B2 | * | 12/2002 | Irrgang et al. ............. 424/70.24 |
| 6,602,494 B1 | * | 8/2003 | Jahedshoar et al. ........ 424/70.1 |
| 2002/0127252 A1 | * | 9/2002 | Kramer et al. .............. 424/401 |
| 2003/0068349 A1 | * | 4/2003 | Jentzsch et al. ............. 424/401 |

FOREIGN PATENT DOCUMENTS

EP 0 927 553 A2 7/1999

OTHER PUBLICATIONS

P.G. Brantom, et al: "A Summary Report of the Colipa International..." Toxicology In Vitro 11 (1997), pp. 141-179.
Ellen Borefreund et al: "Toxicity Determined In Vitro..." Toxicology Letters, 24, 1985, pp. 119-124.

* cited by examiner

*Primary Examiner*—Gregory Webb
(74) *Attorney, Agent, or Firm*—Michael J. Striker

(57) ABSTRACT

The preferably optically clear, transparent or translucent micromulsion contains from 20 to 60 percent by weight water; from 3 to 20 percent by weight of an oil phase, which contains hydrophobic oil that is liquid at 25° C. and optionally dissolved lipophilic materials, and from 20 to 60 percent by weight of an emulsifier mixture. The emulsifier mixture contains at least one first emulsifier, which is an ethoxylated castor oil and/or an ethoxylated hydrogenated castor oil, and at least one second emulsifier with an $NRU_{50}$ value greater than 110 μg/ml. The microemulsion is usable as a cosmetic, dermatological or pharmaceutical preparation, especially as an agent for hair treatment.

20 Claims, No Drawings

MICROEMULSIONS, ESPECIALLY FOR SKIN OR HAIR TREATMENT

BACKGROUND OF THE INVENTION

1. Field of the Invention

The subject matter of the present invention is a microemulsion, which is usable, especially as a cosmetic, dermatological or pharmaceutical agent for skin or hair treatment, preferably in the form of an optically clear, transparent or at least translucent product. This microemulsion contains water, an oil phase comprising liquid hydrophobic oils and an emulsifier mixture of at least two selected emulsifiers.

2. Related Art

Microemulsions are macroscopically homogeneous, optically transparent, low viscosity, thermodynamically stable mixtures comprising two non-miscible liquids and at least one nonionic or ionic surfactant, which contain two hydrophobic groups. If an ionic surfactant containing only one hydrophobic group is added to both components, which are insoluble in each other, e.g. water and nonpolar hydrocarbon, a co-surfactant, usually a short chain aliphatic alcohol, is needed to form a microemulsion. A microemulsion is a ternary mixture of water, hydrophobic phase and surfactant phase. Microemulsions have been shown to be structured with submicroscopic strongly fluctuating bi-continuous oil and water domains with a transmission electron microscope. The sizes of the domains between 3 and 100 nm are stabilized by the boundary surface tension between water-rich and oil-rich phases in the presence of a saturated monomolecular surfactant layer. Frequently microemulsions are solid or semi-solid and have a behavior known as the "ringing effect". Many pharmaceutical and cosmetic preparations are microemulsions. A general problem with microemulsions is that they have a high risk of skin incompatibility, especially skin and eye irritation, in comparison to normal (macro)-emulsions built up from the same recognized safe ingredients. The problem with using especially mild and skin friendly surfactants is that they do not provide sufficient stability and turbidity, separation or color changes can occur. Alternatively the desired hardness or solidity of the product may change or degrade with time.

SUMMARY OF THE INVENTION

It is an object of the present invention to provide a microemulsion, which especially is both skin and eye compatible and which has sufficient long-time stability and a desired clarity and solidity, which does not degrade substantially over a long time interval.

It has now been found that this object is attained by a microemulsion of the following composition. The subject matter of the invention is a preferably an optically clear, transparent or translucent microemulsion containing (A) from 20 to 60 percent by weight, preferably 30 to 55 percent by weight, water;

(B) from 3 to 20 percent by weight of an oil phase, comprising hydrophobic oil that is liquid at 25° C., which can contain dissolved lipophilic materials; and (C) from 20 to 60 percent by weight of an emulsifier mixture, which comprises (c1) at least one first emulsifier, which is selected from the group consisting of ethoxylated castor oils and ethoxylated hydrogenated castor oils; and (c2) at least one second emulsifier, which has an $NRU_{50}$ value greater than 110 µg/ml, and which preferably has an $NRU_{50}$ value, which is greater than that of an ethoxylated hydrogenated castor oil ethoxylated with 40 mol ethylene oxide.

Aqueous Phase (A)

One or more hydrophilic co-solvents, e.g. cosmetically compatible univalent or multivalent alcohols, can be present in the aqueous phase besides water. Suitable polyvalent alcohols are especially those with 1 to 4 carbon atoms, e.g. ethanol or isopropanol. Suitable multivalent alcohols are especially those with 2 to 6 carbon atoms, such as ethylene glycol or propylene glycol, glycerol but also sorbitol, of which glycerol is especially preferred. The co-solvents are preferably used in an amount of from 0 to 15 percent by weight or of 1 to 10 percent by weight. Also dissolved hydrophilic effective and additive ingredients can be contained in the aqueous phase.

Oil Phase (B)

The microemulsion according to the invention contains 3 to 20 percent by weight of an oil phase, preferably from 5 to 15 percent by weight. The oil phase comprises liquid ingredients, which are liquid at room temperature (25° C.) and if necessary dissolved lipophilic effective and additive ingredients. Solid waxes are either not contained, or only contained in an amount that does not impair optical clarity, especially in amounts less than 5 percent by weight, preferably less than one percent by weight.

The liquid oils include, e.g., plant oils, animal oils, mineral oils, silicon oils, hydrocarbon oils, hydrogenated polyolefins, liquid alcohols with at least 8 carbon atoms, especially branched alcohols, such as guerbeta alcohols, oils from fatty acids and polyols, oils from fatty acids and monovalent $C_1$- to $C_{30}$-alcohols, preferably $C_3$- to $C_{22}$-alcohols or mixtures thereof. Suitable oils are especially cycloparaffins, paraffin oils, polydecene, mineral oils, isohexadecane, dodecane, isoeicosane, liquid polydimethylsiloxane, cyclotetrasiloxane, cyclopentasiloxane, phenyltrimethicone, isocetyl palmitate, isopropyl myristate, isopropyl palmitate, isopropyl stearate, octyl isostearate, octylcocoate, octyl palmitate, octyl dodecyl myristate, caprylic/capric triglyceride, butyl octanol, hexyl octanol, butyl decanol, hexyl decanol, octyl dodecanol, hexyl decanol, stearyl heptanoate, isohexyl decanoate, isodecyl octanoate, dibutyl adipate, dicarpylyl ether, $C_{12}$- to $C_{15}$-alkyl benzoate, hydrogenated polyisobutene, squalane, squalene, native oils, such as jojoba oil, olive oil, sun flower seed oil, soy bean oil, peanut oil, colza oil, almond oil, palm oil, coconut oil, castor oil, wheat germ coil, grape-seed oil, thistle oil, candle oil, macademia nut oil, corn seed oil, avocado oil and the like.

Emulsifier (C)

The microemulsion according to the invention contains 20 to 60 percent by weight of the emulsifier, preferably 30 to 50 percent by weight. The weight ratio of the emulsifier (c1) to emulsifier (c2) amounts to preferably from 1:1 to 6:1, especially of 2:1 to 4:1. The emulsifier phase comprises the above-mentioned emulsifier types (c1) and (c2). Especially emulsifiers with $NRU_{50}$ values less than 110 µg/ml are either not contained in the microemulsion, or only contained in small amounts so that the $NRU_{50}$ value of the microemulsion is greater than 110 µg/ml, preferably greater than 200 µg/ml or greater than 750 µg/ml. Emulsifiers with $NRU_{50}$ values less than 110 µg/ml, such as ethoxylated fatty alcohols or ethoxylated fatty alcohol phosphate esters, are not contained or only contained in amounts less than 5 percent by weight or less than 1 percent by weight.

Comparatively large emulsifier amounts are required to make the microemulsions. Conventional microemulsions have a high eye irritation potential because of the large amounts of emulsifiers. It has been shown that the known in-vitro test describes as the Neutral Red Uptake test is sufficiently suitable to characterize the eye irritation ability of microemulsions. Also the $NRU_{50}$ values are suitable to identify suitable emulsifiers for making eye-compatible microemulsions.

The NRU test, which is described in E. Borenfreund, J. A. Puerner, Toxicology Letters 24 (1985), pp. 119-124, is a cytotoxicity test performed with cell cultures. Improved predictions of eye irritation potential are obtained using cells of human HaCaT keratinocyte cell lines instead of the animal BALB/c 3T3 fibroblast cell cultures described in the above-mentioned article.

$NRU_{50}$ values are the NRU values used in the present invention. They characterize the concentration of a substance or composition, at which the up-take of the dye neutral red is reduced to about 50% in human keratinocyte cells. Neutral red (3-amino-7-dimethylamino-2-methyl phenazine hydrochloride) is a weak cationic dye, which easily diffuses from an outer medium through a cell membrane separating individual cells into the cell interior. Changes in the cell surface or the cell membrane by potentially harmful substances reduce the dye uptake and the retention of the dye in the cell. A high $NRU_{50}$ value means a slight cell-damaging action and low cytotoxicity and is a hint of an improved eye compatibility of the tested substance or composition.

Emulsifier (c1) Based on Castor Oil

The first emulsifier is preferably contained in the microemulsion in an amount of 10 to 50 percent by weight, especially of 15 to 45 percent by weight. The first emulsifier is selected from the ethoxylated castor oils and ethoxylated hydrogenated castor oils. The ethoxylation degree can be from 10 to 100, especially from 20 to 60. Suitable materials are those with an INCI name PEG-x castor oil and PEG-x hydrogenated castor oil, wherein x is the ethoxylation degree, e.g. hydrogenated PEG-25 castor oil, hydrogenated PEG-35 castor oil, hydrogenated PEG-40 castor oil, hydrogenated PEG-45 castor oil, hydrogenated PEG-54 castor oil or hydrogenated PEG-60 castor oil.

Co-Emulsifier (c2)

The second emulsier (c2) is contained in the microemulsion in an amount of 3 to 30 percent by weight, especially from 5 to 20 percent by weight. The second emulsifier is preferably selected from fatty acid sugar esters and ethoxylated fatty acid monoglycerides, in which the fatty acids preferably have 8 to 30, especially 12 to 22 carbon atoms. The sugar component of the fatty acid sugar ester is e.g. sucrose. Fatty acid sugar esters are, e.g., those with the INCI name sucrose cocoate, sucrose dilaurate, sucrose distearate, sucrose laurate, sucrose myristate, sucrose oleate, sucrose palmitate, sucrose ricinoleate, and sucrose stearate.

Ethoxylated fatty acid monoglycerides are, e.g., those of the general formula: $C_nH_{(2n+1)}$—CO—OCHCH(—OH)CH$_2$(—OCH$_2$CH$_2$—)$_m$OH, in which n is a whole number, which preferably is from 7 to 29, especially from 11 to 21 and m is number, which gives the ethoxylation degree, which amounts to from 2 to 100, especially from 3 to 40 or from 5 to 12. Fatty acid monoglycerides are, e.g., those with the INCI names PEG-x glyceryl cocoate, PEG-x glyceryl isosterate, PEG-x glyceryl laurate, PEG-x glyceryl oleate, PEG-x glyceryl ricinoleate, PEG-x glyceryl sequioleate, PEG-x glyceryl stearate, PEG-x glyceryl talowate, wherein x gives the ethoxylation degree.

Effective Ingredient

Preferred embodiments of the microemulsion according to the invention contain at least one effective ingredient, which can be a hair cosmetic, skin cosmetic, dermatological and/or pharmaceutical effective ingredient. Effective ingredients are, e.g., multivalent alcohols, UV-filters, light-protecting agents, antioxidants, radical trapping agents, anti-flaking effective ingredients, perfume ingredients, diagnostic agents, therapeutic agents, vitamins, de-fatting agents, vegetable extracts, plant extracts, protein hydrolyzates, silk hydrolyzates, hair luster imparting agents, hair-fixing or hair care nonionic, anionic, cationic, zwitterionic or amphoteric polymers, in which the polymers can be of synthetic or natural original, as well as combinations thereof. The amount of the effective ingredient included in the composition can be varied according to its effectiveness and application purpose, e.g. from 0.001 to 10 percent by weight.

The product according to the invention furthermore can contain the standard cosmetic additive ingredients, e.g. preservatives, bactericides and fungicide effective ingredients, such as e.g. 2,4,4-trichloro-2-hydroxydiphenyl ether, parabene or methyl chloroisothiazolinone, in an amount of about 0.01 to 1.0 percent by weight, buffer substances, such as sodium citrate or sodium phosphate, in an amount of about 0.1 to 1.0 percent by weight, coloring substances, e.g. fluorescein sodium salt, in an amount of about 0.1 to 1.0 percent by weight.

Preferred Embodiment

A preferred embodiment of the microemulsion contains (A) 20 to 60 percent by weight water;

(B) 3 to 20 percent by weight of an oil phase comprising hydrophobic oil that is liquid at 25° C., which is selected from the group consisting of plant oils, animal oils, mineral oils, silicone oils, hydrocarbon oils, oils from fatty acids and polyols, oils from fatty acids and monovalent $C_1$- to $C_{30}$-alcohols or mixture of the above-mentioned oils, in which the oil phase can contain dissolved lipophilic materials and no or less than 5 percent by weight of wax that is solid at room temperature;

(C) 20 to 60 percent by weight of an emulsifier mixture, which comprises at least 90 percent by weight, based on the total amount of the emulsifier present, of (c1) at least one first emulsifier, which is at least one ethoxylated hydrogenated castor oil with an ethoxylation degree of 10 to 80, and (c2) at least one second emulsifier, which is at least one fatty acid sugar ester and at least one ethoxylated fatty acid monoglyceride.

The microemulsion according to the invention can be use according to its composition as a cosmetic agent, topical dermatological agent or a pharmaceutical agent, e.g. as a hair treatment agent, a hair styling agent, hair care agent, skin cream, skin protecting cream, day cream, night cream, sun-protecting agent for skin or hair or as foundation for pharmaceutical preparations.

Application Method

The subject matter of the present invention also include a method for hair treatment, in which a hair treatment agent consisting or comprising microemulsion according to the invention is prepared and then applied to hair and the hair is put in a hair-do or hairstyle.

The hair treatment agent with the microemulsion can be applied to dry or slightly moist hair. The amount of the hair treatment agent used can be a pea-sized or hazelnut-sized amount according to the hair abundance and the desired effect. Preferably this amount of the hair treatment agent is rubbed into the hand surface prior to application to the hair. The product is especially easily distributed in the hair without great effort because of its special consistency. It imparts firmness, definition, structure and hold to the hair. The hair as a pleasant appearance and is lustrous, especially neither dull nor oily. The product is outstandlingly suitable for creative fashioned and re-fashioned modern hairstyles.

The composition according to the invention is especially characterized by its clarity and transparency. Thus the composition is preferably also filled in a corresponding optical package made from transparent or translucent material. Especially glass and transparent or translucent plastic, such as polyethylene, polypropylene or polyethylene terephthalate can be used as the container material.

The following examples further illustrate the subject matter of the invention, but their details should not be considered to limit the appended claims.

EXAMPLES

The determination of the NRU values is based on the standard test methods and the standard performance protocol described in E. Borenfreund, J. A. Puerner, Toxicology Letters 24 (1985), pp. 119-124, modified for COLIPA International Validation Study on Alternatives to the Draize Rabbit Eye Irritation Test (Brantom, et al, 1997) with the following changes: Use of human keratinocyte cell line HaCaT instead of the BALB/c 3T3 mouse fibroblasts and treatment in serum-free culture media.

The neutral red (3-amino-7-dimethylamino-2-methyl phenazine hydrochloride) taken up by the cells exposed to the test substance is extracted and measured spectrophotometrically at 540 nm. Toxicological effects cause a reduction in the amount of taken-up neutral red in comparison to separate untreated control cells. The concentration of the test substance, which leads to a reduction of the up-taken and bound neutral red amount of about 50% in comparison to the control cells, is the $NRU_{50}$-value.

The HaCaT cells are grown in Dulbecco's modified Eagle's medium with 2 mM L-glutamin, 10% (v/v) foetal calf serum (FCS), 100 IU penicillin and 100 µg/ml streptomycin added in an atmosphere having 95% humidity and 5% $CO_2$. A cell stock is stored in equal parts of $1\text{-}2*10^6$ cells/ml in DMEM with 20% FCS and 10% dimethylsulfoxide in the frozen state (−196° C., liquid nitrogen).

To perform the NRU test the cells are grown next in a culture medium for 24 hours and then exposed to the test substance in serum-free keratinocyte culture medium (keratinocyte growth medium KGM), with a modified MCDB 153 formula, of a manufacturer (Clonetics) added with 0.1 ng/ml epidermal growth factor, 5 µg/ml insulin, 0.5 µg/ml hydrocortisone, 0.15 mM $Ca^{++}$, 0.4% v/v bovine pituitary extract (7.5 mg/ml) and antibiotics.

In pretests an approximate $NRU_{50}$ value is determined with 8 different concentrations of the test substance. On this basis eight suitable concentrations around these approximate values are selected for the final measurements. The measurement is repeated with an independent batch with equal concentrations. Sodium lauryl sulfate with concentrations of 50, 25, 10 and 1 µg/ml is used as reference substance.

Approximately $2*10^4$ HaCaT cells in 250 µl growth medium per receptacle are placed in 60 central receptacles of microtiter plates each with 96 receptacles. The corner receptacles act as controls and contain only the growth medium. The plates are incubated for 24 hours at 37° C. in a moist atmosphere with 5% $CO_2$ and 95% air. The culture medium is removed and either replaced by pure treatment medium or by treatment medium containing the various concentration of the test substance to be tested or the reference substance. The layout of the microtiter plate is shown in the following table I.

TABLE I

MICROTITER PLATE LAYOUT

| | 1 | 2 | 3 | 4 | 5 | 6 | 7 | 8 | 9 | 10 | 11 | 12 |
|---|---|---|---|---|---|---|---|---|---|---|---|---|
| A | BC | BC | BC | BC | BC | BC | BC | BC | BC | BC | BC | BC |
| B | BC | CC | TI1 | TI1 | TI1 | TI1 | TI2 | TI2 | TI2 | TI2 | CC | BC |
| C | BC | CC | TI3 | TI3 | TI3 | TI3 | TI4 | TI4 | TI4 | TI4 | CC | BC |
| D | BC | CC | TI5 | TI5 | TI5 | TI5 | TI6 | TI6 | TI6 | TI6 | CC | BC |
| E | BC | CC | TI7 | TI7 | TI7 | TI7 | TI8 | TI8 | TI8 | TI8 | CC | BC |
| F | BC | CC | R1 | R1 | R1 | R1 | R2 | R2 | R2 | R2 | CC | BC |
| G | BC | CC | R3 | R3 | R3 | R3 | R4 | R4 | R4 | R4 | CC | BC |
| H | BC | BC | BC | BC | BC | BC | BC | BC | BC | BC | BC | BC |

BC: blank control, contain 250 µl of pure KGM (serum-free keratinocyte culture medium).
CC: contain control cells (negative controls).
TI1 to TI8: contain cells in KGM with eight different concentrations of the test substance.
R1 to R4: contain cells in KGM with 4 different concentrations of the reference substance (sodium lauryl sulfate).

After an acting time of 24 hours the treatment medium is replaced by storage medium, which contains 50 μg/ml of neutral red. The plates are placed again in the incubator for three hours. After that the medium is removed, the cells washed with a fixative (1% formaldehyde, 1% calcium chloride) and 100 μl of an extraction solution (1% acetic acid in 50% ethanol) is added to each receptacle for dye extraction. After 20 minutes the absorption is measured at 540 nm with a microplate reader. Concentration/effectiveness diagrams are drawn or plotted, expressed as percent viability of the negative control cells (CC) relative to the respective test concentrations from the average values and after correction with the null value from the BC receptacles. The $NRU_{50}$ value, which represents the concentration of the test substance, at which the neutral red uptake is reduced to about 50% relative to the negative controls, is determined by interpolation of the obtained graphs of the concentration/effectiveness. The obtained value is acceptable, when the value obtained for the reference substance, sodium lauryl sulfate, is in a range of 10 to 30 μg/ml.

The NRU values given in the following are $NRU_{50}$ values in units of μg/ml determined by the above-described methods.

Emulsifiers according to the invention:

CREMOPHOR® RH 410: PEG-40 Hydrogenated Castor Oil;

$NRU_{50}$=188 μg/ml

CREMOPHOR® CO60: PEG-60 Hydrogenated Castor Oil;

$NRU_{50}$=203 μg/ml

CETIOL® HE: PEG-7 Glyceryl Cocoate; $NRU_{50}$=249 μg/ml

TEGOSOFT® LSE 65K: Sucrose Cocoate; $NRU_{50}$=198 μg/ml

Emulsifiers not according to the invention:

EUMULGIN® 05: Oleth-5; NRU=7.8

EUMULGIN® B2: Ceteareth-20; NRU=5.8

VOLPO® N20: Oleth-20; NRU=6.2

Example 1

Amounts in g—$NRU_{50}$ in μg/ml

TABLE II

EXEMPLARY MICROEMULSIONS WITH THEIR $NRU_{50}$ VALUES

|  | A | B | C | D | E |
|---|---|---|---|---|---|
| PEG-40 hydrogenated castor oil | 30 | 30 | 30 | 30 | 30 |
| PEG-7 Glyceryl cocoate | 10 | 10 | 10 | 10 | 10 |
| Sucrose cocoate | 10 | — | — | — | — |
| Octyl dodecanol | — | — | — | — | 10 |
| Caprylic/capric Triglyceride | 10 | 5 | 3.3 | 10 | — |
| Glycerol | — | 5 | 3.3 | — | — |
| Propylene glycol | — | — | 3.3 | — | — |
| Panthenol | 0.1 | 0.1 | 0.1 | 0.1 | 0.1 |
| Preservative, UV filter, perfume | q.s. | q.s. | q.s. | q.s. | q.s. |
| Water | To 100 | To 100 | To 100 | To 100 | To 100 |
| $NRU_{50}$ | 1334 | 1184 | 976 | 2216 | 256 |

TABLE III

EXEMPLARY MICROEMULSIONS WITH THEIR $NRU_{50}$ VALUES

|  | F | G | H | I | J |
|---|---|---|---|---|---|
| PEG-40 hydrogenated castor oil | — | 20 | 20 | 20 | 20 |
| PEG-60 hydrogenated castor oil | 20 | — | — | — | — |
| Sucrose cocoate | 10 | 10 | 10 | 10 | 10 |
| PEG-7 Glyceryl cocoate | — | — | — | 10 | — |
| Ceteareth-20 | 10 | — | 10 | — | — |
| Oleth-5 | — | 10 | — | — | 10 |
| Oleth-20 | — | — | — | 10 | 10 |
| Octyl dodecanol | — | — | 10 | 10 | — |
| Caprylic/capric Triglyceride | 10 | 10 | — | — | 10 |
| Panthenol | 0.1 | 0.1 | 0.1 | 0.1 | 0.1 |
| Preservative, UV filter, perfume | q.s. | q.s. | q.s. | q.s. | q.s. |
| Water | To 100 | To 100 | To 100 | To 100 | To 100 |
| $NRU_{50}$ | 51 | 83 | 53 | 30 | 36 |

Comparative Examples

Commercial Products

| Product | $NRU_{50}$ [μg/ml] |
|---|---|
| Tec ni art Digit Gloss (L'Oreal): Aqueous phase: water, propylene glycol, glycerol Oil Phase: $C_{12}$- to $C_{15}$-alkyl benzoate, octyldodecyl neopentanoate Emulsifiers: PEG-40 Hydrogenated castor oil, PPG-5-ceteth-20, Steareth-20, Oleth-3 phosphate | 22 |
| TRENDLINE gel was normal (Goldwell): Aqueous phase: water, sorbitol, butylene glycol, glycerol Oil Phase: Paraffin liquidum Emulsifiers: Oleth-5, Oleth-3, phosphate, ceteareth-20 | 71 |
| Shape Up Soft Wax (Schwarzkopf) Aqueous phase: water, sorbitol, butylene glycol, glycerol Oil phase: paraffinum liquidum Emulsifiers: Oleth-5, Oleth-3 phosphate | 59 |

The disclosure in German Patent Application P10 2004 004 394.9 of Jan. 29, 2004 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a microemulsion, especially for skin and hair treatment, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A microemulsion containing an aqueous phase and an oil phase, and
from 20 to 60 percent by weight water;
from 3 to 20 percent by weight of said oil phase, said oil phase comprising hydrophobic oil that is liquid at 25° C. and optionally dissolved lipophilic materials; and from 20 to 60 percent by weight of an emulsifier mixture; wherein said emulsifier mixture consists essentially of least one first emulsifier and at least one second emulsifier; and wherein said at least one first emulsifier is selected from the group consisting of ethoxylated castor oils and ethoxylated hydrogenated castor oils and said at least one second emulsifier has an $NRU_{50}$ value greater than 110 µg/ml.

2. The microemulsion as defined in claim 1 wherein said hydrophobic oil comprises at least one member selected from the group consisting of plant oils, animal oils, mineral oils, silicone oils, hydrocarbon oils, hydrogenated polyolefins, liquid alcohols with at least 8 carbon atoms, oils from fatty acids and polyols, oils from fatty acids and monovalent $C_1$- to $C_{30}$-alcohols, or mixtures thereof.

3. The microemulsion as defined in claim 1, wherein said oil phase contains no wax solid at room temperature in an amount that impairs optical clarity.

4. The microemulsion as defined in claim 1, wherein said at least one first emulsifier has an ethoxylation degree of from 10 to 100.

5. The microemulsion as defined in claim 1, wherein said at least one first emulsifier is selected from the group consisting of hydrogenated PEG-25 castor oil, hydrogenated PEG-35 castor oil, hydrogenated PEG-40 castor oil, hydrogenated PEG-45 castor oil, hydrogenated PEG-54 castor oil and hydrogenated PEG-60 castor oil.

6. The microemulsion as defined in claim 1, wherein said at least one second emulsifier is selected from the group consisting of fatty acid sugar esters and ethoxylated fatty acid monoglycerides.

7. The microemulsion as defined in claim 1, wherein said at least one second emulsifier is sucrose cocoate and/or ethoxylated glyceryl cocoate.

8. The microemulsion as defined in claim 1, wherein a weight ratio of said at least one first emulsifier to said at least one second emulsifier is in a range from 1:1 to 6:1.

9. The microemulsion as defined in claim 1, wherein said emulsifier mixture does not contain any emulsifier with an $NRU_{50}$ value of less than or equal to 110 µg/ml or only contains said any emulsifier in an amount of less than 10 percent by weight, based on a total weight of the microemulsion.

10. The microemulsion as defined in claim 1, further comprising at least one hair cosmetic skin cosmetic, dermatological and/or pharmaceutical effective ingredient.

11. The microemulsion as defined in claim 10, wherein said at least one effective ingredient is selected from the group consisting of multivalent alcohols, UV-filters, light-protecting agents, antioxidants, radical trapping agents, anti-flaking agents, perfumes, diagnostic agents, therapeutic agents, vitamins, de-fatting agents, vegetable extracts, plant extracts, protein hydrolyzates, silk hydrolyzates, hair luster imparting agents, hair-fixing polymers and hair care polymers, as well as combinations thereof.

12. A microemulsion containing an aqueous phase and an oil phase, and from 20 to 60 percent by weight water;

from 3 to 20 percent by weight of said oil phase comprising hydrophobic oil that is liquid at 25° C., said hydrophobic oil being at least one member selected from the group consisting of plant oils, animal oils, mineral oils, silicone oils, hydrocarbon oils, oils from fatty acids and polyols, oils from fatty acids and monovalent $C_1$- to $C_{30}$-alcohols; or mixtures of the foregoing oils, said oil phase optionally containing dissolved lipophilic materials and no, or less than 5 percent by weight, of wax that is solid at room temperature;

from 20 to 60 percent by weight of an emulsifier mixture, which consists essentially of at least 90 percent by weight of at least one first emulsifier and at least one second emulsifier, based on a total emulsifier amount present, said at least one first emulsifier being at least one ethoxylated hydrogenated castor oil with an ethoxylation degree of 10 to 80 and said at least one second emulsifier being at least one fatty acid sugar ester and/or at least one ethoxylated fatty acid; and in which a weight ratio of said at least one first emulsifier to said at least one second emulsifier is in a range from 1:1 to 6:1.

13. A pharmaceutical, dermatological or cosmetic composition comprising said microemulsion as defined in claim 1.

14. A method of hair treatment, said method comprising the steps of:

a) preparing a hair treatment composition containing or consisting of a microemulsion, said microemulsion containing an aqueous phase, an oil phase, from 20 to 60 percent by weight water, from 3 to 20 percent by weight of said oil phase, which comprises hydrophobic oil that is liquid at 25° C. and optionally dissolved lipophilic materials, and from 20 to 60 percent by weight of an emulsifier mixture, and in which said emulsifier mixture consists essentially of at least one first emulsifier and at least one second emulsifier, said at least one first emulsifier is selected from the group consisting of ethoxylated castor oils and ethoxylated hydrogenated castor oils, and said at least one second emulsifier has an $NRU_{50}$ value greater than 110 µg/ml;

b) applying said hair treatment composition to hair; and c) setting or putting the hair in a hair-do or hair style.

15. A cosmetic product for hair treatment, said cosmetic product consisting of:

a translucent or transparent package; and a clear, transparent hair treatment composition contained in the translucent or transparent package;

in which said clear transparent hair treatment composition contains or consists of a microemulsion, said microemulsion containing an aqueous phase and an oil phase, and from 20 to 60 percent by weight water;

from 3 to 20 percent by weight of said oil phase, which comprises hydrophobic oil that is liquid at 25° C. and optionally dissolved lipophilic materials; and from 20 to 60 percent by weight of an emulsifier mixture;

in which said emulsifier mixture consists essentially of at least one first emulsifier and at least one second emulsifier; and wherein said at least one first emulsifier is selected from the group consisting of ethoxylated castor oils and ethoxylated hydrogenated castor oils and said at least one second emulsifier has an $NRU_{50}$ value greater than 110 µg/ml.

16. The cosmetic product as defined in claim 15, wherein said translucent or transparent package is made of glass or a translucent or transparent plastic material.

17. The cosmetic product as defined in claim 15, wherein said translucent or transparent package is made of a translucent or transparent plastic material selected from the group consisting of polyethylene, polypropylene and polyethylene terephthalate.

18. The microemulsion as defined in claim 1, wherein said emulsifier mixture consists of said at least one first emulsifier and said at least one second emulsifier, a weight ratio of said at least one first emulsifier to said at least one second emulsifier is in a range from 1:1 to 6:1, said at least one first emulsifier is ethoxylated hydrogenated castor oil with an ethoxylation degree of from 20 to 60, and said at least one second emulsifier is at least one fatty acid sugar ester in which the fatty acid group has 12 to 22 carbon atoms and/or at least one ethoxylated fatty acid monoglyceride of the general formula (I):

(I), in which n is a whole number from 11 to 21 and m is an integer from 5 to 12.

19. The microemulsion as defined in claim 1, wherein said emulsifier mixture consists of said at least one first emulsifier and said at least one second emulsifier, a weight ratio of said at least one first emulsifier to said at least one second emulsifier is in a range from 1:1 to 6:1, said at least one first emulsifier is hydrogenated PEG-35 castor oil, hydrogenated PEG-40 castor oil, or hydrogenated PEG-45 castor oil, and said at least one second emulsifier is an ethoxylated glyceryl cocoate with an ethoxylation degree from 5 to 12.

20. The microemulsion as defined in claim 1, wherein said emulsifier mixture consists of said at least one first emulsifier and said at least one second emulsifier, a weight ratio of said at least one first emulsifier to said at least one second emulsifier is from 1:1 to 6:1, said at least one first emulsifier is an ethoxylated hydrogenated castor oil with an ethoxylation degree of 40, said at least one second emulsifier is ethoxylated glyceryl cocoate with an ethoxylation degree of 7, and said oil is caprylic/capric triglyceride.

* * * * *